United States Patent [19]

Todd et al.

[11] 4,291,693

[45] Sep. 29, 1981

[54] FLUID METERING DEVICE

[75] Inventors: Robert J. Todd; Terry M. Wonder, both of Salt Lake City, Utah

[73] Assignee: Sorenson Research Company, Inc., Salt Lake City, Utah

[21] Appl. No.: 93,422

[22] Filed: Nov. 13, 1979

[51] Int. Cl.³ ............................................. A61M 5/16
[52] U.S. Cl. ............................. 128/214 C; 128/214.2; 73/215; 137/551; 222/40; 222/159
[58] Field of Search ............ 128/214 R, 214 C, 214.2; 73/194 R, 198, 215, 216; 222/23, 40, 159; 137/551

[56] References Cited

U.S. PATENT DOCUMENTS

| | | | |
|---|---|---|---|
| 2,479,786 | 10/1945 | Stevens | 73/216 |
| 2,842,123 | 7/1958 | Rundhaug | 128/214 |
| 3,001,397 | 9/1961 | Leonard | 73/194 |
| 3,049,918 | 3/1960 | Sparkuhl | 73/209 |
| 3,233,457 | 2/1966 | Martinez | 73/198 |
| 3,340,871 | 9/1967 | Jellies | 128/214 |
| 3,460,526 | 8/1969 | McKirdy et al. | 128/2.05 |
| 3,521,635 | 7/1970 | Koehn | 128/214 C |
| 3,533,400 | 10/1970 | Palich | 128/2.05 |
| 3,690,318 | 9/1970 | Gorsuch | 128/214 E |
| 3,730,168 | 9/1970 | McWhorter | 128/2 F |
| 3,803,914 | 4/1974 | Noiles | 73/209 |
| 3,807,389 | 4/1974 | Miller et al. | 128/2.05 D |
| 3,850,348 | 11/1974 | Bessot et al. | 222/386.5 |
| 3,877,428 | 4/1975 | Seagle et al. | 128/214 R |
| 3,929,157 | 12/1975 | Serur | 137/453 |
| 3,980,082 | 9/1976 | Miller | 128/214 R |
| 4,043,322 | 8/1977 | Blumberg et al. | 128/214 E |
| 4,136,692 | 1/1979 | Goldowsky | 128/214 C |

*Primary Examiner*—Stephen C. Pellegrino
*Attorney, Agent, or Firm*—H. Ross Workman; Rick D. Nydegger

[57] ABSTRACT

A method and apparatus for metering fluids that are parenterally administered to a patient. The fluid metering device consists of a plastic housing having a primary fluid channel formed therein that is in fluid communication with a fluid source. A secondary fluid channel is also formed in the housing and is connected at one end to the primary fluid channel so as to be in fluid communication therewith. Fluid flows through the primary fluid channel and through a fixed resistor that is in series with the primary fluid channel. The fluid then flows through a drip tube in series with the fixed resistor. From the drip tube, the fluid is collected in a drip chamber. The secondary fluid channel is vented into the drip chamber so that the pressure at the open end of the stationary fluid channel will be the same as the pressure in the drip chamber. Thus, the fixed resistor will cause the fluid to back up, entering the secondary fluid channel. Because the pressure in the secondary fluid channel is the same as the pressure in the drip chamber, the level of fluid in the secondary fluid channel will be proportional to the rate of fluid flow. The rate of fluid flow through the primary fluid channel may therefore be read directly from the level of fluid in the secondary fluid channel.

22 Claims, 5 Drawing Figures

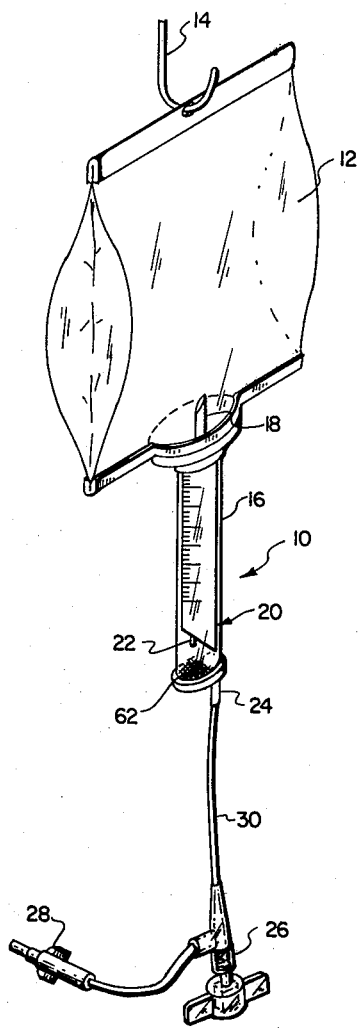
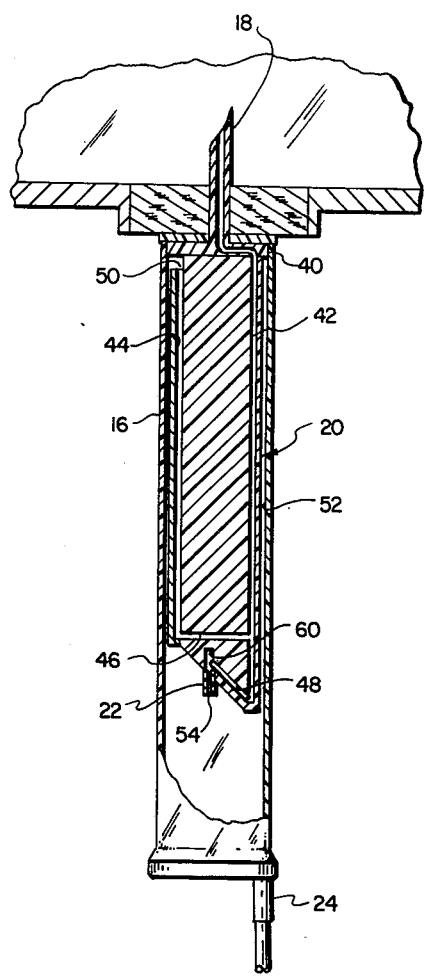
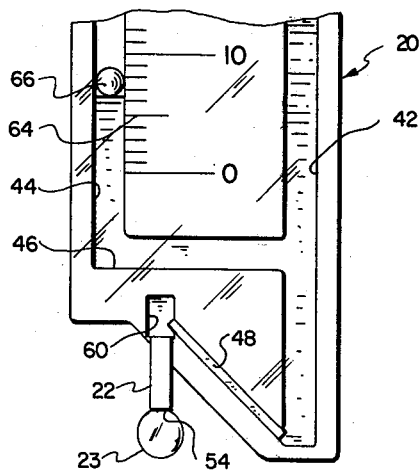
Fig. 1
Fig. 2
Fig. 3

FLUID METERING DEVICE

BACKGROUND

1. Field of the Invention

The present invention relates to flow meters, and more particularly to a combination flow meter and drip chamber used for measuring the flow rate of fluids parenterally administered to a patient.

2. The Prior Art

Intravenous infusion of fluids into a patient has long been a commonplace hospital procedure. Typically, intravenous infusion apparatus consists of an indwelling catheter that is connected through tubing to a fluid source such as an elevated plastic bag.

Because of the importance of knowing the exact amount of fluid being received intravenously by a patient, it is necessary to frequently monitor the flow rate of the infusion fluid. This is typically accomplished by the use of a drip chamber. A drip generating source in direct communication with the fluid source allows the fluid to be released as drops into a drip chamber. A predetermined volume per drop is determined by the size of the opening of the drip generator. Thus by counting the drops over a period of time one can calculate the flow rate using the predetermined volume per drop.

Drip chambers are advantageous because they provide a readily visible indication that fluid is flowing through the system to the patient. However, in the past, one of the problems associated with drip chambers has been the excessive time consumed in the procedure of counting the drops and calculating the flow rate. Not only is this procedure time consuming, but it is subject to human error in miscounting the drops or miscalculating the flow rate.

In some kinds of situations it is of utmost importance to provide a carefully controlled flow rate for the infusion fluid. For example, proper administration of some types of medication may require continuous infusion at carefully controlled flow rates over extended periods of time.

Thus, various types of metering devices have ben developed in order to avoid the potential for inaccuracy that is inherent with conventional type drip chambers, as described above. For example, see U.S. Pat. Nos. 4,043,322, 3,877,428, 3,807,389, 3,690,318 and 3,233,457.

Although these various types of metering devices may improve the safety and accuracy of metering parenterally administered fluids, they are much more complex and more expensive to build than conventional drip chambers. Moreover, many of them do not provide the type of easily visible inspection that is available with a drip chamber.

Thus, what is needed is a combination flow meter and drip chamber that is inexpensive and that eliminates the potential for inaccuracy of a conventional drip chamber and which still provides the same type of ready visibility as a drip chamber. Such an invention is illustrated and described herein.

BRIEF DESCRIPTION AND OBJECTS OF THE INVENTION

The metering device of the present invention is a combination flow meter and drip chamber that provides for continuous, instantaneous reading of the flow rate of a parenterally administered fluid.

The combination flow meter and drip chamber includes a transparent housing having a series of fluid channels and a drip generator formed therein. A primary fluid channel in the housing receives the infusion fluid and is in fluid communication with a secondary fluid channel formed in the housing. The primary fluid channel is also in fluid communication with a fixed resistor and a drip tube which empties into a drip chamber. In one embodiment of the invention, the drip chamber forms an airtight enclosure about the housing. In a second embodiment of the invention, the drip chamber forms an airtight enclosure only about that portion of the housing that contains the drip generator formed by the fixed resistor and drip tube. The secondary fluid channel is vented into the drip chamber so that the pressure at the open end of the secondary fluid channel will be the same as the pressure in the drip chamber. Thus, the fluid entering the secondary fluid channel will rise to a level that is directly proportional to the rate of fluid flow through the primary fluid channel and drip generator. A graduated scale may be placed on the housing adjacent the secondary fluid channel so that the flow rate may be read directly with reference to the level of fluid in the secondary fluid channel.

It is therefore a primary object of the present invention to provide an improved metering device for measuring the flow rate of fluids that are parenterally administered to a patient.

Another important object of the present invention is to provide an inexpensive metering device in combination with a drip chamber.

Yet another object of the present invention is to provide a combination flow meter and drip chamber having a primary fluid channel through which an infusion fluid flows into a drip chamber and a secondary fluid channel that is maintained at the same pressure as the drip chamber so that the level of fluid therein will vary in proportion to the rate of fluid flow through the primary fluid channel.

A further object of the present invention is to provide a combination flow meter and drip chamber that is simple in its construction and economical to manufacture.

These and other objects of the present invention will become more fully apparent from the following description and appended claims taken in conjunction with the accompanying drawing.

BRIEF DESCRIPTION OF THE DRAWING

FIG. 1 is a perspective illustration of the metering device of the present invention as used in conjunction with a fluid source and conventional tubing designed to be interconnected to an indwelling catheter in a patient.

FIG. 2 is a partial cross-sectional view of the metering device of FIG. 1.

FIG. 3 is an enlarged view particularly illustrating the base of the housing used in the metering device of FIG. 1.

DETAILED DESCRIPTION OF THE PREFERRED EMBODIMENTS

Figure 4:
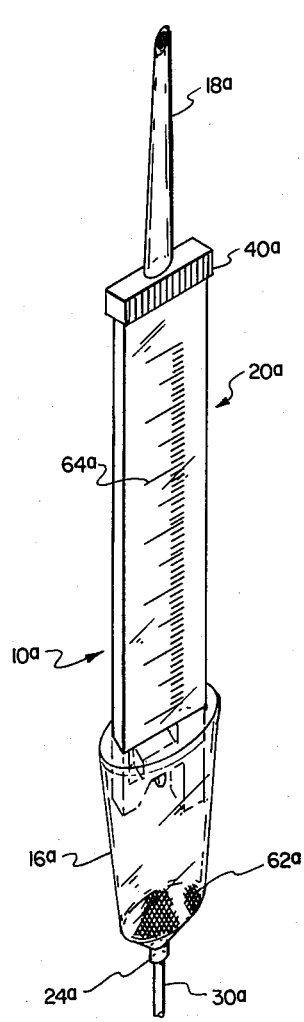
FIG. 4 is a perspective illustration of a second embodiment of the metering device of the present invention.

Reference is now made to the drawing wherein like parts are designated with like numerals throughout.

1. The Embodiment of FIGS. 1-3

The metering device of the present invention may be used with a variety of different types of intravenous infusion apparatus. For purposes of illustration the metering device generally designated 10 has been shown in FIG. 1 in conjunction with a fluid supply bag 12 which is typically made of a flexible material and is suspended from a stand 14. The metering device 10 is generally connected directly to the fluid supply bag 12 so as to allow the fluid from the bag to pass through inlet 18.

As illustrated in FIG. 1, metering device 10 is connected through an outlet tube 24 to tubing 30. Tubing 30 is in turn connected to a variable flow restrictor device 26. In the illustrated embodiment, the variable flow restrictor 26 is a needle valve that may be operated to either increase or decrease the flow rate as desired. It will of course be appreciated that any suitable flow restrictor could be used, as for example a pinch clamp or a roller clamp. The variable flow restrictor 26 and tubing 30 may be interconnected through a conventional luer fitting 28 to a catheter (not shown) inserted into a patient (not shown).

As further illustrated in FIG. 1, the metering device 10 is provided with a cylindrical drip chamber 16 which encloses a housing generally designated 20. As hereinafter more fully described, housing 20 has a plurality of fluid channels formed therethrough. The fluid channels meter the flow rate as the fluid passes through the housing 20. From housing 20, the fluid passes through a drip tube 22 into the cylindrical drip chamber 16 that surrounds housing 20.

Drip chamber 16 is constructed from plastic or other flexible transparent material so that the housing may be squeezed in order to fill the metering device 10 with fluid when setting the flow rate to a particular level. Transparency of drip chamber 16 and housing 20 permits ready visibility of the fluid flowing through the metering device 10.

The configuration of housing 20 is best illustrated in FIG. 2. Housing 20 is enclosed by drip chamber 16, and is mounted at its upper end to a plastic plug 40 which forms an airtight seal with drip chamber 16. A series of fluid channels formed through housing 20 direct the incoming fluid received through inlet 18.

The fluid is first received by primary fluid channel 42 which is in direct fluid communication with inlet 18. As shown best in FIG. 3, primary fluid channel 42 joins connecting fluid channel 46, thus allowing fluid passing through the primary fluid channel 42 to continue through the channel 42 or to be diverted through connecting fluid channel 46. A secondary fluid channel 44 is connected at one end thereof to fluid channel 46. The other end of secondary fluid channel 44 (see FIG. 2) is vented through a throughbore 50 into the annular space 52 formed by drip chamber 16 about housing 20.

With particular reference to FIG. 3, a fixed resistor 48 is in fluid communication with the lower end of primary fluid channel 42. Fixed resistor 48 consists of a small stainless steel tube that is oriented so that the fluid passing therethrough will move upwardly, thus helping to avoid trapping any bubbles in the resistor 48.

From resistor 48, fluid enters a small chamber 60 that functions as a bubble trap. Fluid then passes through drip tube 22 into the lower portion of drip chamber 16. A fine mesh screen 62 (see FIG. 1) is placed in the bottom of drip chamber 16 to prevent bubbles from entering the tubing 30 that leads to the patient (not shown).

In practice, it has been found that the size of drip tube 22 should be selected so that the size of each drop 23 (see FIG. 3) will be large enough to create only a slight resistance to flow. For example, drip tube 22 may have an inside diameter of 0.059 in. (0.150 cm) and an outside diameter of 0.072 in. (0.183 cm).

The slight resistance created by the drop size causes a slight bounce in the fluid level in secondary channel 44 each time a drop 23 is released. This slight bounce is desirable because it helps to prevent the fluid in channel 44 from adhering to the sides of the channel 44, which would result in an inaccurate reading of the fluid level, as described in more detail below.

With continued reference to FIG. 3, a graduated linear scale 64 is placed on housing 20 adjacent to the secondary fluid channel 44. Secondary fluid channel 44 contains a float 66 that marks the level of the fluid in channel 44. Secondary fluid channel 44 may also be enclosed along its length with glass or plastic that is designed to magnify the contents of the fluid channel 44, thus making it easier to read the fluid level in reference to the scale 64.

The length of scale 64 is dependent upon the degree of resistance created by the fixed resistor 48. For example, for a resistor having a length of 0.484 in. (1.23 cm) and a diameter of 0.021±0.00025 in. (0.533±0.0064 mm), scale 64 will read from 0 to 250 ml/hr on a linear scale that is 1.97 in. (5.0 cm) in length. By increasing or decreasing the resistance of resistor 48, the length of scale 64 may be expanded or reduced as desired.

The manner of operating the combination flow meter and drip chamber will be readily apparent to those of ordinary skill in the art. First, inlet 18 is coupled to the fluid source 12 (see FIG. 1). Luer fitting 28 is then coupled to the portion of tubing 30 that leads to the catheter (not shown) which is inserted into the patient (not shown).

The metering device is initially primed by squeezing drip chamber 16 and then releasing the drip chamber so as to fill the system with fluid. Fluid is then allowed to flow through inlet 18 into primary fluid channel 42. Fluid flows through primary fluid channel 42 into fixed resistor 48. Resistor 48 impedes the flow of fluid therethrough and thus causes the fluid to enter the secondary fluid channel 44 through connecting channel 46 (see FIG. 3).

Since the secondary fluid channel is vented at its upper end (see FIG. 2) through throughbore 50 into the drip chamber 16, fluid will rise in the secondary channel 44 until the pressure in drip chamber 16 is in equilibrium with the pressure in fluid channel 44. Thus, the level of fluid in secondary channel 44 will be proportional to the fluid flow rate through primary fluid channel 42. The flow rate may thus be read directly from the level of fluid in secondary channel 44 as referenced by the float 66 and scale markings 64.

2. The Embodiment of FIGS. 4-5

Figure 5:
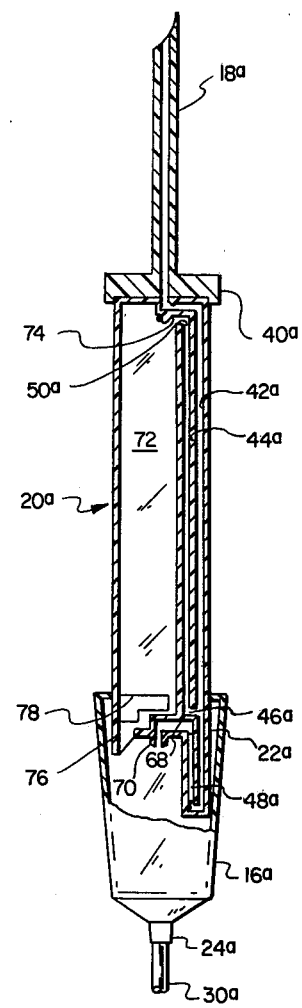
FIG. 5 is a partial cross-sectional view of the metering device of FIG. 4.

The combination flow meter and drip chamber illustrated in FIGS. 4 and 5 differs from the embodiment of FIGS. 1-3 primarily in the internal construction of the housing 20a and in the position of the drip chamber 16a with respect to housing 20a.

As illustrated in FIG. 5, housing 20a has a primary fluid channel 42a that is in direct fluid communication with inlet 18a. A secondary fluid channel 44a communicates through connecting channel 46a to primary fluid channel 42a.

As with the embodiment of FIGS. 1-3, the metal tube 48a provides a fixed resistance through which fluid from primary fluid channel 42a must pass. From the fixed resistor 48a, fluid enters an enlarged channel 68 and then passes through drip tube 70 into drip chamber 16a.

Like the embodiment of FIGS. 1-3, the drip tube 70 is sized so as to provide a slight resistance when a drop forms at the orifice thereof, creating a bouncing effect on the level of fluid contained in the secondary fluid channel 44a. Fixed resistor 48a may also be sized in the manner previously described so that the scale 64a (see FIG. 4) may be expanded or reduced to a desired length.

With further reference to FIG. 5, it will be seen that housing 20a has an enlarged overflow and vent chamber 72 situated adjacent to secondary fluid channel 44a. An opening 74 is provided at the upper end of secondary fluid channel 44a. The opening 74 permits excess fluid to flow into chamber 72 and through the exit port 76 into drip chamber 16a.

The overflow and vent chamber 72 is also provided at its base with an enlarged opening 78. Opening 78 permits the chamber 72 to be vented into drip chamber 16a so that the pressure in the secondary fluid chamber 44a will be maintained in equilibrium with the pressure in drip chamber 16a.

The operation of the metering device of FIGS. 4 and 5 is essentially the same as the embodiment previously described in connection with FIGS. 1-3. After priming the system by squeezing the drip chamber 16a, fluid begins to enter primary fluid chamber 42a from inlet 18a. As the fluid from primary fluid channel 42a reaches the fixed resistor 48a, the fluid flow is impeded and the fluid begins to back up, entering secondary fluid channel 44a. The level of fluid in secondary fluid channel 44a will continue to rise until the pressure in secondary fluid channel 44a creates the desired flow through fixed resistor 48a. As previously described, the level of fluid in secondary fluid channel may readily be determined in reference to the scale 64a, thereby indicating the rate of fluid flow through primary fluid channel 42a.

The combination flow meter and drip chamber illustrated in FIGS. 4 and 5 differs from the embodiment of FIGS. 1-3 primarily in the position of the drip chamber 16a with respect to the housing 20a.

From the foregoing, it will be appreciated that the combination flow meter and drip chamber of the present invention advantageously permits continuous, instantaneous and accurate measurement of the flow rate of a parenterally administered fluid, while at the same time allowing for the continuous observation of fluid flow through a drip chamber. The combination flow meter and drip chamber is simple in its construction and operation and is light in weight so that it may be easily connected to the fluid line.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A fluid metering device comprising:

a drip chamber;
a primary fluid channel in fluid communication with a fluid source;
a secondary fluid channel vented into said drip chamber and connected at one end thereof to said primary fluid channel so as to be in fluid communication therewith; and
a drip generator, said drip generator comprising (1) a fixed resistor means in fluid communication with said primary fluid channel, said fixed resistor means being situated so as to cause the fluid flowing therethrough to flow essentially upwardly through said resistor means, and (2) a drip forming means in series with said fixed resistor means, whereby the level of fluid in said secondary fluid channel will vary in proportion to the rate of fluid flow through said drip generator.

2. A fluid metering device as defined in claim 1 wherein said primary fluid channel, said secondary fluid channel, and said generator are contained in a plastic housing.

3. A fluid metering device as defined in claim 2 wherein said drip chamber forms an airtight enclosure that surrounds said housing.

4. A fluid metering device as defined in claim 2 wherein said drip chamber forms an airtight enclosure about essentially only that portion of said housing that contains said drip generator.

5. A fluid metering device as defined in claim 4 wherein said housing has a combination overflow and vent chamber formed therein which terminates in said airtight enclosure formed by said drip chamber.

6. A fluid metering device as defined in claim 2 wherein said housing is provided with a graduated scale for indicating the fluid flow rate by the level of fluid in said secondary fluid channel.

7. A fluid metering device as defined in claim 6 wherein the portion of said housing that contains said secondary fluid channel is configurated so as to magnify the contents of said secondary fluid channel thereby facilitating the reading of said fluid level in the secondary fluid channel.

8. A fluid metering device as defined in claim 7 further comprising a float situated in said secondary fluid channel, said float facilitating the reading of said fluid level in the secondary fluid channel.

9. A fluid metering device as defined in claim 6 wherein said resistor means is sized so as to permit said graduated scale to read from 0 to 250 ml/hr on a linear scale that is approximately 5 cm in length.

10. A fluid metering device as defined in claim 1 further comprising a variable flow restrictor means placed in line with said drip generator, said flow restrictor means varying the rate of fluid flow through said drip generator.

11. A fluid metering device as defined in claim 1 wherein said drip chamber is formed from flexible plastic so that the drip chamber may be squeezed in order to rapidly fill said fluid channels with fluid.

12. A fluid metering device as defined in claim 1 further comprising a screen placed in said drip chamber, said screen preventing bubbles from leaving the drip chamber.

13. A device for metering the flow of parenterally administered fluids, the device comprising:

a flexible drip chamber;
a housing, said housing having formed therein a primary fluid channel in fluid communication with a fluid source, a secondary fluid channel vented into said drip chamber and connected at one end thereof to said primary fluid channel so as to be in fluid communication therewith, a fixed resistor means in fluid communication with said primary fluid channel, said fixed resistor means being situated so as to cause the fluid flowing therethrough to flow essentially upwardly through said resistor means, and a drip forming means in series with said fixed resistor means, whereby the level of fluid in said secondary channel will vary in proportion to the rate of fluid flow through said fixed resistor means and said drip forming means; and a variable flow restrictor means in line with said drip chamber, said variable flow restrictor means being operable to vary the rate of fluid flow through said fixed resistor means and said drip forming means.

14. A metering device as defined in claim 13 wherein said drip chamber forms an airtight enclosure that surrounds said housing.

15. A metering device as defined in claim 13 wherein said drip chamber forms an airtight enclosure about essentially only that portion of said housing that contains said drip generator.

16. A metering device as defined in claim 15 wherein said housing has a combination overflow and vent chamber formed therein which terminates in said airtight enclosure formed by said drip chamber.

17. A metering device as defined in claim 13 wherein said fixed resistor means comprises a metal tube having a small throughbore, said tube being situated in said housing such that the fluid flowing through said primary channel will be forced to flow in an upward direction through the throughbore of said tube.

18. A metering device as defined in claim 17 further comprising a graduated scale placed on said housing adjacent said secondary fluid channel.

19. A metering device as defined in claim 18 wherein the portion of said housing that covers said secondary fluid channel is configured so as to magnify the contents of said secondary fluid channel thereby facilitating the reading of said fluid level in relation to said graduated scale.

20. A metering device as defined in claim 19 further comprising a float placed in said secondary fluid channel, said float indicating the level of fluid in relation to said graduated scale.

21. A device for metering the flow of parenterally administered fluids, the device comprising:

a plastic housing, said housing having formed therein a primary fluid channel in fluid communication with a fluid source, a secondary fluid channel vented through a throughbore at one end thereof into a drip chamber and connected at the other end thereof to said primary fluid channel so as to be in fluid communication therewith, a fixed resistor means in fluid communication with said primary fluid channel, said fixed resistor means being situated so as to cause the fluid flowing therethrough to flow essentially upwardly through said resistor means, and a drip tube in series with said fixed resistor means, whereby the level of fluid in said secondary channel will vary in proportion to the rate of fluid flow through said fixed resistor means and said drip tube;

a drip chamber forming an airtight enclosure about said housing, said drip chamber being constructed from flexible plastic so that said drip chamber may be squeezed in order to rapidly fill said fluid channels with fluid;

a variable flow restrictor means placed in line with said drip chamber, said variable flow restrictor means being operable to vary the rate of fluid flow through said fixed resistor means and said drip tube;

a graduated scale comprising a plurality of markings placed on said housing adjacent said secondary fluid channel, each said marking corresponding to a different rate of fluid flow;

a float placed in said secondary fluid channel for indicating the level of fluid in relation to said graduated scale; and means for magnifying the contents of said secondary fluid channel so as to facilitate reading of the fluid level in relation to said graduated scale.

22. A device for metering the flow of parenterally administered fluids, the device comprising:

a plastic housing, said housing having formed therein a primary fluid channel in fluid communication with a fluid source, a combination overflow and vent channel, a secondary fluid channel communicating at one end thereof with said overflow and vent channel and connected at the other end thereof to said primary fluid channel so as to be in fluid communication therewith, an outlet port for said overflow and vent channel, and a fixed resistor means in fluid communication with said primary fluid channel, said fixed resistor means being situated so as to cause the fluid flowing therethrough to flow essentially upwardly through said resistor means, whereby the level of fluid in said secondary fluid channel will vary in proportion to the rate of fluid flow through said fixed resistor means;

a drip chamber forming an airtight enclosure about the portion of said housing that contains said drip tube and said outlet port for said overflow and vent channel, the drip chamber being constructed from flexible plastic in order to permit the fluid contained in the drip chamber to be rapidly flushed therefrom by squeezing the drip chamber; and a graduated scale comprising a plurality of markings placed on said housing adjacent said secondary fluid channel, each said marking corresponding to a different rate of fluid flow.

* * * * *